United States Patent
Cabilly et al.

(10) Patent No.: US 7,824,532 B2
(45) Date of Patent: *Nov. 2, 2010

(54) APPARATUS AND METHOD FOR ELECTROPHORESIS

(75) Inventors: Shmuel Cabilly, Gedera (IL); Uri Yogev, Yavne (IL); Ilana Margalit, Ramat Gan (IL)

(73) Assignee: Life Technologies Corporation, Carlsbad, CA (US)

( * ) Notice: Subject to any disclaimer, the term of this patent is extended or adjusted under 35 U.S.C. 154(b) by 708 days.

This patent is subject to a terminal disclaimer.

(21) Appl. No.: 10/056,050

(22) Filed: Jan. 28, 2002

(65) Prior Publication Data

US 2002/0112960 A1     Aug. 22, 2002

Related U.S. Application Data (63) Continuation-in-part of application No. 08/734,929, filed on Oct. 22, 1996, now Pat. No. 6,379,516, which is a continuation-in-part of application No. 08/639,869, filed on Apr. 26, 1996, now Pat. No. 5,865,974, which is a continuation-in-part of application No. 08/427,917, filed on Apr. 26, 1995, now Pat. No. 5,582,702.

(51) Int. Cl.
    *G01N 27/26*         (2006.01)
    *G01N 27/30*         (2006.01)
(52) U.S. Cl. .................. 204/456; 204/466; 204/468; 204/606; 204/616
(58) Field of Classification Search ......... 204/456–470, 204/606–621
See application file for complete search history.

(56) References Cited

U.S. PATENT DOCUMENTS

| | | | |
|---|---|---|---|
| 3,062,731 A | | 11/1962 | Durrum |
| 3,715,295 A | | 2/1973 | Tocci |
| 3,764,513 A | | 10/1973 | Saravis |
| 3,888,759 A | * | 6/1975 | Elson et al. ................. 204/620 |
| 3,948,743 A | * | 4/1976 | Monthony et al. .......... 204/469 |
| 3,951,776 A | * | 4/1976 | Eibl et al. ................ 422/82.01 |
| 4,018,662 A | | 4/1977 | Ruhenstroth-Bauer et al. |
| 4,130,471 A | | 12/1978 | Grunbaum |
| 4,219,395 A | | 8/1980 | Smith et al. |

(Continued)

FOREIGN PATENT DOCUMENTS

EP          155 977          10/1985

(Continued)

OTHER PUBLICATIONS

U.S. Appl. No. 09/651,087, filed Aug. 30, 2000, Cabilly et al.

(Continued)

*Primary Examiner*—Jeffrey T Barton (57) ABSTRACT

Apparatus for conducting electrophoresis therein includes a chamber with a gel matrix. The chamber has a first sealed region and a second sealed region, and an anode within the first sealed region of the chamber and in contact with the gel matrix, and a cathode within the second sealed region and in contact with the gel matrix. At least one of the electrodes also provides ions for driving the electrophoresis. The apparatus further includes a matrix with at least one sparingly water-soluble salt.

50 Claims, 4 Drawing Sheets

U.S. PATENT DOCUMENTS

| | | | |
|---|---|---|---|
| 4,305,799 A | 12/1981 | Schwarz et al. | |
| 4,323,439 A | 4/1982 | O'Farrell | |
| 4,773,984 A * | 9/1988 | Flesher et al. | 204/618 |
| 4,874,491 A | 10/1989 | Stalberg | |
| 4,892,639 A | 1/1990 | Sarrine et al. | |
| 4,908,112 A * | 3/1990 | Pace | 210/198.2 |
| 5,006,473 A | 4/1991 | Bouma et al. | |
| 5,045,164 A | 9/1991 | Tansamrit et al. | |
| 5,082,548 A | 1/1992 | Faupel et al. | |
| 5,106,477 A | 4/1992 | Coleman | |
| 5,209,831 A | 5/1993 | MacConnell | |
| 5,407,552 A | 4/1995 | Lebacq | |
| 5,411,657 A | 5/1995 | Leka | |
| 5,464,516 A | 11/1995 | Takeda et al. | |
| 5,464,517 A | 11/1995 | Hjerten et al. | |
| 5,582,702 A | 12/1996 | Cabilly et al. | |
| 5,656,145 A | 8/1997 | Nguyen et al. | |
| 5,785,835 A | 7/1998 | Saito et al. | |
| 5,843,295 A | 12/1998 | Steiner et al. | |
| 5,865,974 A | 2/1999 | Cabilly et al. | |
| 5,972,188 A | 10/1999 | Rice et al. | |
| 6,013,166 A | 1/2000 | Heller | |
| 6,056,860 A | 5/2000 | Amigo et al. | |
| 6,068,752 A | 5/2000 | Dubrow et al. | |
| 6,071,396 A | 6/2000 | Day | |
| 6,096,182 A | 8/2000 | Updyke et al. | |
| 6,113,766 A | 9/2000 | Steiner et al. | |
| 6,232,076 B1 | 5/2001 | Schulz | |
| 6,379,516 B1 | 4/2002 | Cabilly et al. | |
| 2002/0134680 A1 | 9/2002 | Cabilly et al. | |

FOREIGN PATENT DOCUMENTS

| | | | |
|---|---|---|---|
| EP | 1 167 962 | 1/2002 | |
| GB | 2284484 * | 6/1995 | 204/616 |
| WO | WO 87/04948 | 8/1987 | |
| WO | WO 94/08234 | 4/1994 | |
| WO | WO 96/18891 | 6/1996 | |
| WO | WO 96/34276 | 10/1996 | |
| WO | WO 97/41070 | 11/1997 | |
| WO | WO 98/10277 | 3/1998 | |
| WO | WO 98/35013 | 8/1998 | |
| WO | WO 00/16084 | 3/2000 | |
| WO | WO 02/18901 | 3/2002 | |
| WO | WO 02/071024 | 9/2002 | |

OTHER PUBLICATIONS

Computer translation of JP 2000-060554.

Abstract of JP 362066153.

A.T. Andrews, "Electrophoresis: Theory, Techniques and Bio-Chemical and Clinical Applications", Chapter 1, Clarendon press, Oxford 1993.

A.T. Andrews, "Electrophoresis: Theory, Techniques and Bio-Chemical and Clinical Applications", p. 79, 2nd Edition, 1986.

Stoyanov A.V. et al., "Properties of buffer systems with charges immobolized on a gel matrix and their potential use in capillary electrophoresis", Journal of Chromatography A, Elsevier Science, NL, vol. 799, No. 1-2, Mar. 13, 1998, pp. 275-282.

Weber G. et al., "Optimized continuous flow electrophoresis", Electrophoresis, Weinheim, DE, vol. 17, No. 12, 1996, pp. 1906-1910.

European Search Report for EP 02 702692, mailed Aug. 2, 2004.

\* cited by examiner

APPARATUS AND METHOD FOR ELECTROPHORESIS

CROSS REFERENCE TO OTHER APPLICATIONS

This application is a continuation in part of U.S. Ser. No. 08/734,929 filed Oct. 22, 1996 now U.S. Pat. No. 6,379,516, which is a continuation in part of U.S. Ser. No. 08/639,869 filed Apr. 26, 1996 now U.S. Pat. No. 5,865,974 which is a continuation in part of U.S. Ser. No. 08/427,917 filed Apr. 26, 1995 now U.S. Pat. No. 5,582,702.

FIELD OF THE INVENTION

The present invention relates to the field of electrophoresis and more particularly to apparatus for conducting electrophoresis tests therein.

BACKGROUND OF THE INVENTION

A great deal of diagnostic procedures and laboratory research are carried out wherein DNA, RNA or proteins are mobilized and/or separated according to their physical and chemical properties via electrophoresis. This process is widely used and has may applications. For example, it is used to analyze DNA molecules according to their resultant size after being digested by restriction enzymes. It is also used to analyze the products of a polymerase chain reaction (PCR).

Typically, electrophoresis separation is carried out in a separation matrix, such as a gel of agarose or acrylamide or a combination of the two. Usually, agarose gels are cast in open trays and form a slab whereas acrylamide gels are cast between two glass plates.

In order to effect the electrophoretic process, two opposite ends of the gels are exposed to a buffer solution, which is connected by electrodes, typically platinum, to an electrical power source. Once the electrical power source is switched on, the electric field forces negatively charged molecules to move towards the anode and positively charged molecules to move towards the cathode. The electrodes that are commonly used for electrophoresis are generally made of inert metals that induce water electrolysis in aqueous solutions, which produces hydroxyl ions at the cathode side and protons at the anode side. Therefore, large volumes of buffer are used in order to maintain the pH. In addition, due to the use of buffers of low salt concentration, large volumes of buffer are required to maintain the electric field.

DNA is negatively charged and therefore, in the agarose or acrylamide gels which provide sieving action, DNA molecules move towards the anode at a rate which depends on their size, wherein the smaller the molecules the faster they move.

In the electrophoretic separation of proteins, the proteins are often treated with an ionic detergent, such as sodium dodecylsulphate (SDS). The negatively charged dodecylsulphate anions interact with hydrophobic domains on the protein molecules, thus creating negatively charged protein/SDS complexes that undergo electrophoresis separation similar to DNA molecules.

Typically, it is desirable to visualize and to document the results of the electrophoretic separation test. In electrophoretic separation of DNA molecules, this has been done by immersing the gel slab after the electrophoretic separation has been completed in a solution of a fluorescent compound which emits visible light when exposed to a ultra violet (UV) light. A widely used compound is ethidium bromide.

Conventional electrophoretic systems are deficient in many respects, a few of which are listed below.

Prior art electrophoresis systems are a potential source of contamination to the working environment in which the tests are performed. The two major sources of contamination are ethidium bromide and PCR products. Ethidium bromide is a hazardous chemical due to its mutagenic activity. In addition, the environment is a potential source of contamination to the system, since PCR is an extremely sensitive method. In fact, a single molecule of DNA product from one PCR (out of the trillions of molecules being produced) may interfere with the subsequent PCR such that it will produce incorrect results.

Conventional electrophoresis is also deficient in other respects, one being that it is time consuming.

Many different gel separation materials have been disclosed, with different compositions, pH characteristics, voltage requirements, etc. The goal of most of the recent innovations in the field has been to provide an electrophoresis gel which can be used to perform a faster, more accurate, more stable, or more versatile electrophoresis separation.

U.S. Pat. No. 4,874,491 to Stalberg discloses an electophoresis system having a high concentration buffer containing gel.

U.S. Pat. No. 4,892,639 to Sarrine et al. discloses an electrophoresis plate with improved buffer circulation.

U.S. Pat. No. 5,045,164 to Tansamrit et al. discloses an electrophoresis plate having thickened ends as buffer reservoirs.

U.S. Pat. No. 5,209,831 to MacConnel discloses a bufferless disposable cassette having open ends and conductive film electrodes.

U.S. Pat. No. 5,407,552 to Lebacq and U.S. Pat. No. 5,411,657 to Leka disclose open electrophoresis devices requiring a buffer tank for operation.

U.S. Pat. No. 6,096,182 to Updyke et al. discloses an electrophoresis gel at a neutral pH. The advantage of producing such a gel is that the gel system is stable, with reduced reactivity and increased shelf life.

SUMMARY OF THE INVENTION

There is provided, in accordance with an embodiment of the present invention, apparatus for conducting electrophoresis, the apparatus including a chamber defining an electrophoresis area, the area including a gel matrix, the chamber further including a sealed region, an anode within the chamber and in contact with the gel matrix, wherein the anode is contained within the sealed region of the chamber, and a cathode within the chamber and in contact with the gel matrix. The sealed region is sealed before and during the electrophoresis.

In various embodiments the anode comprises an electrochemical ionizable conducting material such as a metal. The metal may be copper, silver, lead, or an oxygen-absorbing material such as album, or carbon, or any other suitable material. Multiple anodes or cathodes may be included. In another embodiment the chamber further includes one or more apertures corresponding to one or more loading sites in the chamber, and the apertures are not included in the sealed region. The apertures may be spaced at predetermined intervals so as to conform with intervals between tips on a loader. In several described embodiments, the apertures may be arranged in one or more rows, and the rows may be arranged in stagger format.

There is provided, in accordance with another embodiment of the present invention apparatus for conducting electrophoresis, the apparatus including a chamber defining an electrophoresis area, the area including a gel matrix, the chamber further including a sealed region; and a cathode within the chamber and in contact with the gel matrix, wherein the cathode is contained within the sealed region of the chamber; and an anode within the chamber and in contact with the gel matrix. In one embodiment, the region is sealed before and during the electrophoresis.

In one embodiment, the apparatus further includes a matrix, wherein the matrix is in contact with the cathode, the matrix including at least one water sparingly soluble salt, the gel matrix including ions, the ions generated during an electrochemical reaction of the matrix in contact with the cathode.

In several embodiments, the cathode is comprised of hydrogen-absorbing material, or may be palladium, carbon, a metal hydride or any other suitable material.

There is provided, in accordance with another embodiment of the present invention apparatus for conducting electrophoresis, the apparatus including a chamber defining an electrophoresis area, the area including a gel matrix, the chamber further including a first and a second sealed regions, an anode within the chamber and in contact with the gel matrix, wherein the anode is contained within the first sealed region of the chamber; and a cathode within the chamber and in contact with the gel matrix, wherein the cathode is contained within the second sealed region of the chamber.

There is provided, in accordance with another embodiment of the present invention an apparatus for conducting electrophoresis the apparatus including, a chamber defining an electrophoresis area, the electrophoresis area having at least one body of a gel matrix for facilitating the electrophoresis, a first electrode and a second electrode. The first electrode and the second electrode are each in contact with the chamber, at least one of the first electrode and the second electrode is embedded within the body of the gel matrix, the first electrode is an anode and the second electrode is a cathode, and the body of the gel matrix includes ions generated during an electrochemical reaction of the anode.

There is provided, in accordance with another embodiment of the present invention an apparatus for conducting electrophoresis. The apparatus includes a chamber defining an electrophoresis area, the electrophoresis area having at least one body of a gel matrix for facilitating the electrophoresis, a first electrode and a second electrode. The fist electrode and the second electrode are in contact with the chamber, and at least one of the first electrode and the second electrode is embedded within the at least one body of the gel matrix. In this embodiment the first electrode is an anode and the second electrode is a cathode, the body of the gel matrix includes electrolyte solution, the anode comprises an electrochemically ionizable metal, and the electrolyte solution is of a composition such that migration of ions generated by the anode during electrophoresis is inhibited.

There is provided, in accordance with another embodiment of the present invention an apparatus for conducting electrophoresis. The apparatus includes a chamber defining an electrophoresis area, the chamber including a sealed region, and the electrophoresis area having at least one body of a gel matrix for facilitating the electrophoresis. The apparatus further includes a first electrode and a second electrode, both in contact with the chamber, wherein at least one of the first and the second electrodes is embedded within the body of gel matrix. The first electrode is an anode and the second electrode is a cathode, the body of gel matrix includes electrolyte solution, the anode is contained within the sealed region of the chamber and comprises an electrochemically ionizable metal, and the electrolyte solution is of a composition such that migration of ions generated by the anode during electrophoresis is inhibited.

There is provided, in accordance with another embodiment of the present invention a method for electrophoresis. The method includes the steps of applying an electrical field to a gel and driving electrophoresis by releasing ions required for maintaining an electrical field by degradation of a metal anode.

In one embodiment the step of driving an electrophoresis does not include water electrolysis.

There is provided, in accordance with another embodiment of the present invention a method for electrophoresis. The method includes the steps of applying an electrical field to the gel and driving electrophoresis by releasing ions required for maintaining an electrical field by degradation of a sparingly water-soluble salt in contact with a cathode.

There is provided, in accordance with another embodiment of the present invention method for electrophoresis. The method includes the steps of applying an electrical field to the gel and driving an electrophoresis by releasing ions required for maintaining an electrical field by degradation of a metal anode and degradation of a sparingly water-soluble salt in contact with a cathode. A further step includes inhibiting migration of ions in the vicinity of the anode.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

The present invention discloses an apparatus for conducting electrophoresis including a chamber defining an electrophoresis area, wherein the chamber is sealed in at least one region. The electrophoresis apparatus of the present invention includes at least one cathode and/or at least one anode which, according to one embodiment, is located in a sealed region of the chamber.

Reference is now made to FIGS. 1-8 which illustrate an electrophoresis disposable cassette, constructed and operative in accordance with preferred embodiments of the present invention. It is noted that like components are designated by like reference numerals throughout the various figures.

Figure 1:
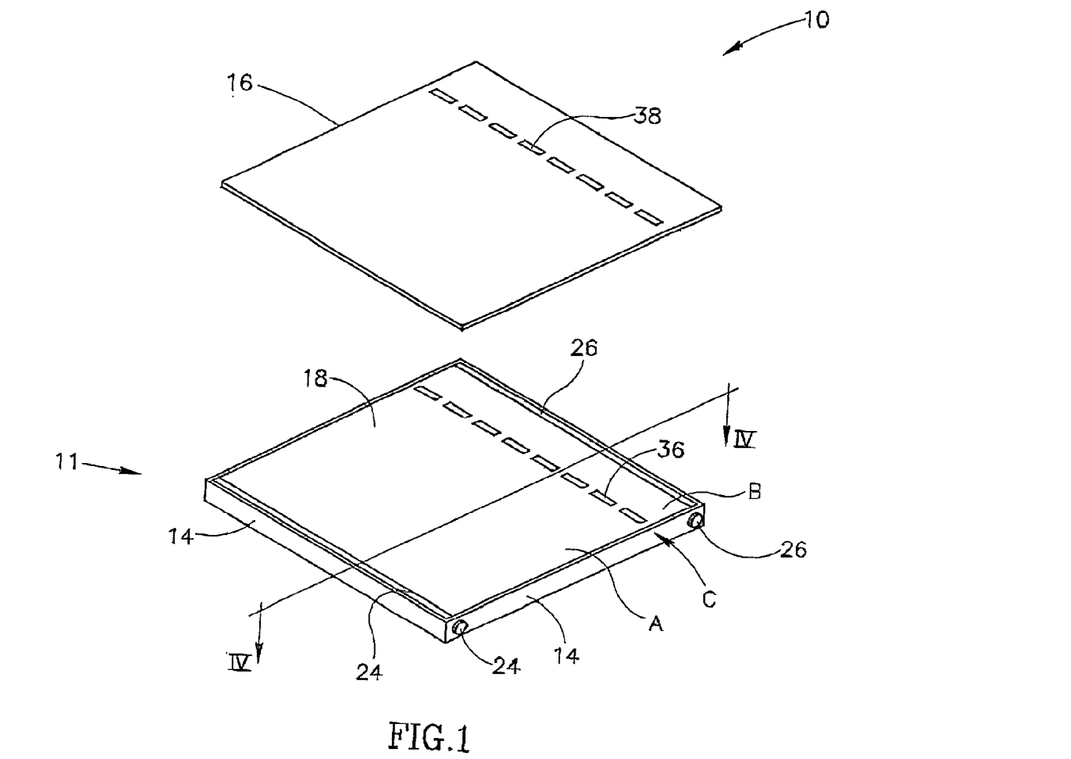
FIG. 1 is a schematic illustration of an electrophoresis cassette, constructed and operative in accordance with a preferred embodiment of the present invention.

Reference is now made to FIG. 1, which shows one embodiment of the present invention. Cassette 10 comprises a three dimensional area 11 having bottom wall and side walls, referenced 12 and 14 respectively, and a top wall 16. Cassette 10 is substantially sealed in that it is enclosed by walls 12, 14 and 16, with the exception of one or more apertures 38 corresponding to one or more loading sites, as will be described hereinbelow.

Bottom wall 12 and top wall 16 are preferably made of any suitable UV transparent material, such as the TPX plastic commercially available from MITSUI of Japan or the Polymethylmethacrylate (PMMA) plastic commercially available from Repsol Polivar S.P.A. of Rome, Italy. Cassette 10 further includes an anode 24 and a cathode 26.

As shown in FIGS. 1-4, cassette 10 is divided into three regions: A, B and C. Region A includes anode 24, and spans the area of cassette 10 between the side wall 14 closest to anode 24 and one end of Region C. Region B includes cathode 26, and spans the area of cassette 10 between the side wall 14 closest to anode 26 and the other end of Region C. Region C comprises the area of cassette 10 with loading sites 36, or wells. Regions A and B comprise no wells, and thus have the potential for being completely sealed. Region C, on the other hand, does comprise wells. Since the wells are connected to apertures 38 within top wall 16, region C is not fully sealed.

Figure 2:
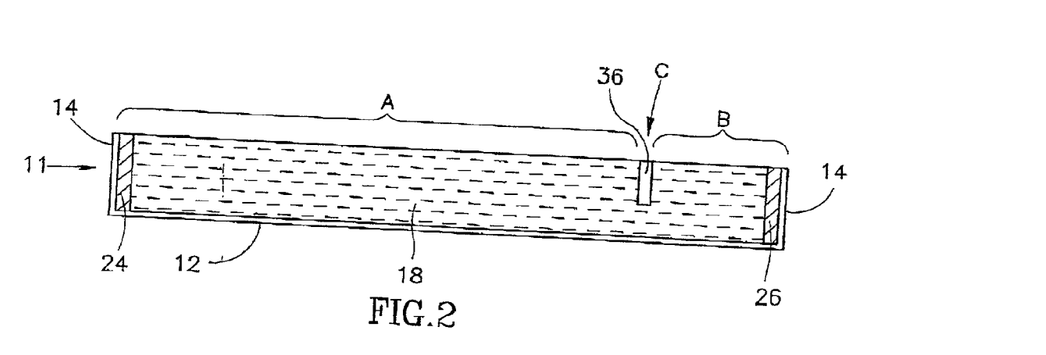
FIG. 2 is a schematic cross section illustration along line IV ill FIG. 1.
Figure 3:
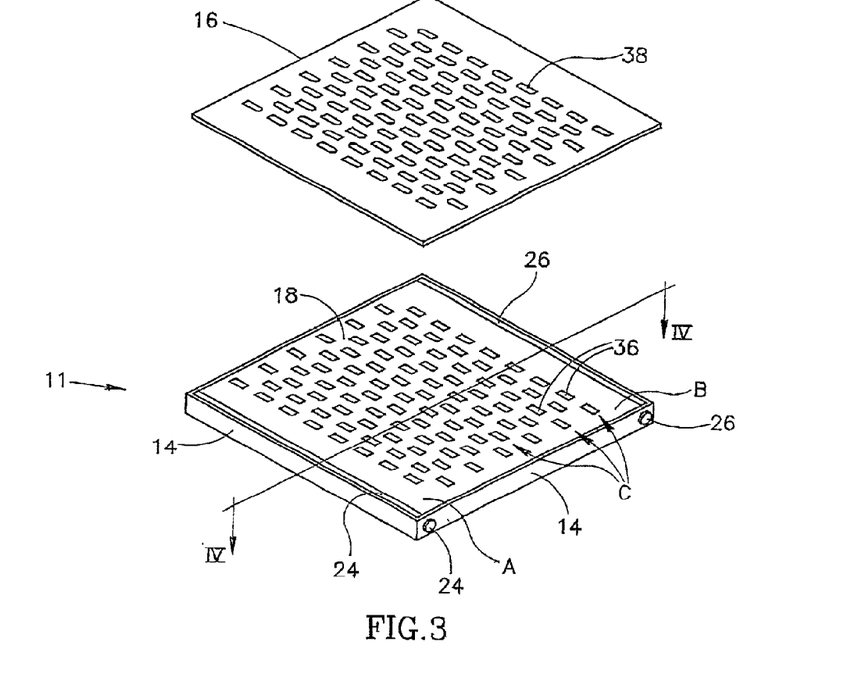
FIG. 3 is a schematic illustration of an electrophoresis cassette including a plurality of apertures arranged in rows and loading sites according to another embodiment of the present invention.
Figure 4:
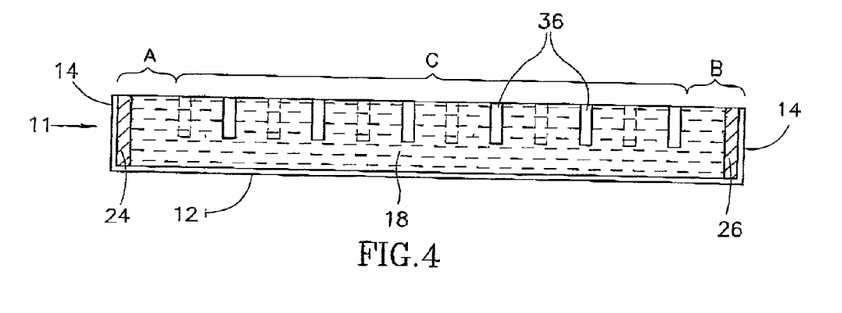
FIG. 4 is a schematic illustration of cross section illustration along line IV in FIG. 3 in accordance with one embodiment of the present invention.
Figure 5:
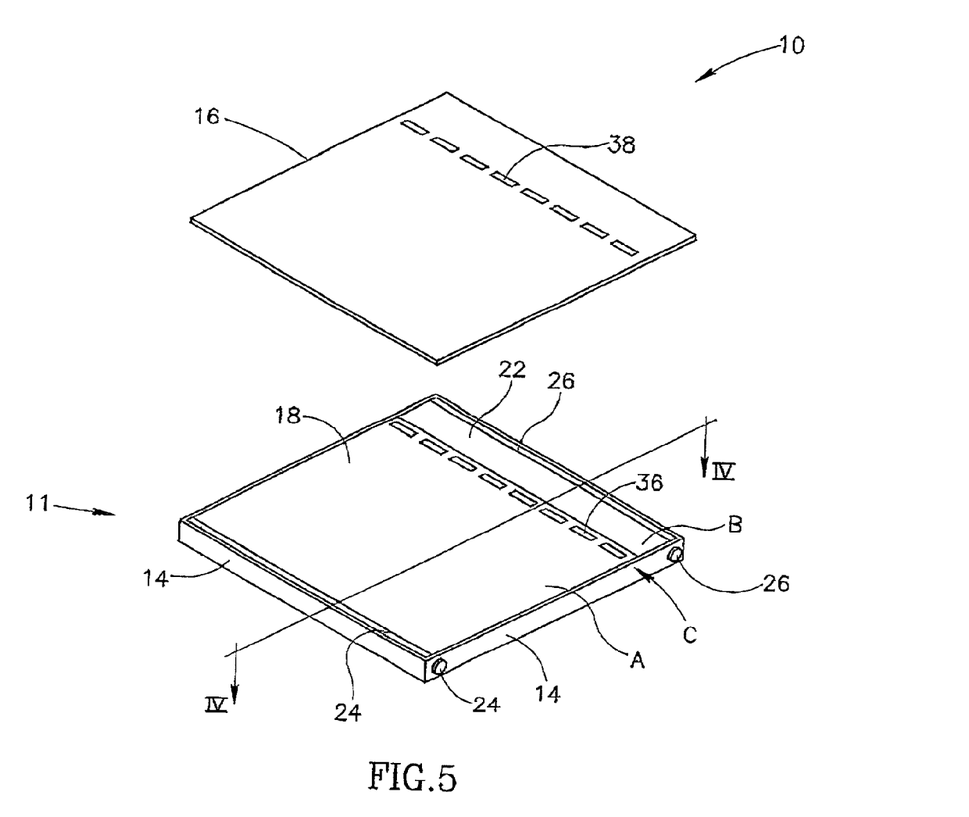
FIG. 5 is a schematic illustration of an electrophoresis cassette including an ion source matrix according to another embodiment of the present invention.
Figure 6:
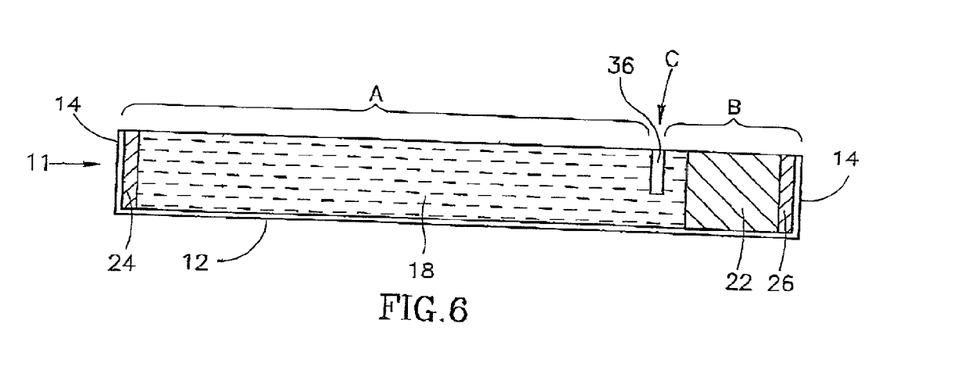
FIG. 6 is a schematic illustration of a cross section illustration along line IV in FIG. 5 in accordance with another embodiment of the present invention.
Figure 7:
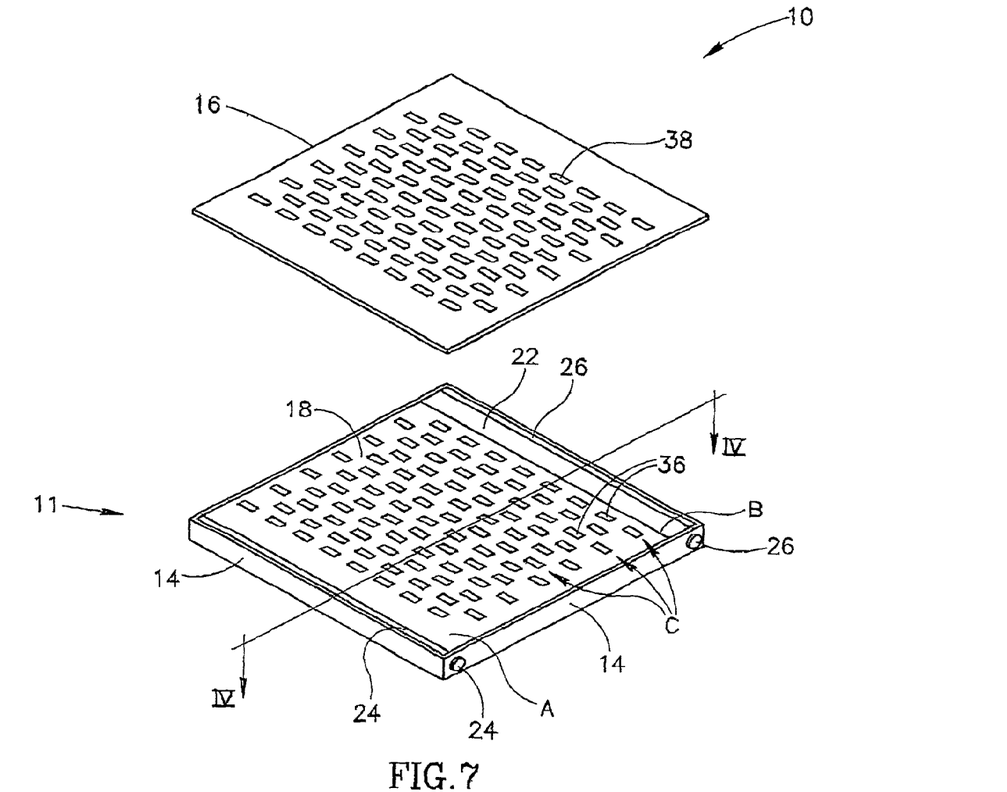
FIG. 7 is a schematic illustration of an electrophoresis cassette including an ion source according to another embodiment of the present invention.
Figure 8:
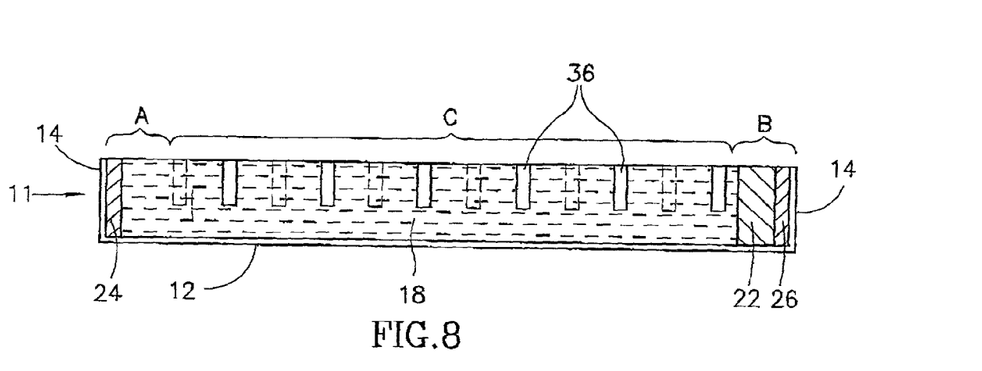
FIG. 8 is a schematic illustration of a cross section illustration along line IV in FIG. 7 in accordance with another embodiment of the present invention.

According to one embodiment, as shown in FIGS. 1 and 2, Region C spans a relatively small area, including loading sites 36, which are in direct alignment with apertures 38 on top wall 16. In a preferred embodiment, Region A comprises a relatively large area, and region B comprises a relatively small area, since loading sites 36 are situated relatively closer to cathode 26. In another embodiment, Region A comprises a relatively small area and region B comprises a relatively large area since loading sites 36 are situated relatively closer to anode 24. In accordance with another embodiment, shown in FIGS. 3 and 4, Region C spans a relatively large area which includes loading sites 36 arranged in predetermined intervals, which are in direct alignment with apertures 38 on top wall 16. In this embodiment, Regions A and B are both relatively small since loading sites 36 span almost the entire gel. It will be appreciated that Regions A or B or both of cassette 10 are totally sealed thereby reducing the possibility of contamination originating therefrom.

As further described in FIGS. 5-8, in another embodiment the chamber comprises at the cathode end an electrode made of a conducting material, e.g., metal (M) and an ion source, matrix 22. Ion source matrix 22 comprises a salt suspended in a suitable matrix e.g. gel matrix, providing ions for driving the electrophoresis. The salt is sparingly soluble in water and has the general formula $Y^{+n}{}_m(X^{-m})_n$, where n is the valency of the cation Y and $X^{-m}$ is an anion having a valency m.

In one preferred embodiment, Y is the metal cation and the salt has the general formula $M^{+n}{}_m(X^{-m})_n$, where n is the valency of the cation of metal M and $X^{-m}$ is an anion having a valency m. Alternatively, M and the cation of the salt are different.

In a preferred embodiment, the cation Y is selected to have suitable electrochemical properties such that when a suitable voltage difference is applied between the cathode 26 and the anode 24, some of the $Y^{+n}$ cations receive electrons from the cathode and become neutral species.

Concomitantly, $X^{-m}$ anions move away from the cathode serving as charge carriers for the current flowing through cassette 10.

In another embodiment, the anode is made of a conductive material which includes metal atoms, and is in contact with or embedded in the body of gel matrix 18. Atoms from the anode lose electrons and serve as charge carriers for the current flowing through the cassettes moving toward the cathode as $A^{+n}$ cations.

An advantage of cassette 10 is that the electrolysis of water at the anode and the cathode ends is substantially avoided, thus obviating the accumulation of gases in the vicinity of the cathode and the anode and the need for vent holes or gas absorbing means. Therefore, the gel matrix 18 according to the present invention is substantially free from hydrogen and/or oxygen in the vicinity of the anode and/or the cathode. Another advantage resulting from obviating electrolysis of water at the anode and the cathode ends is that there is substantially no production or buildup of hydroxyl and hydrogen ions at the cathode and the anode, respectively, Thus, the pH remains generally constant during the electrophoretic separation.

It will be appreciated that the anode metal electrode 24 in cassette 10 can be made of different metals having suitable electrochemical properties wherein during an electrophoresis run, the electrochemical reaction wherein metal atoms of the metal electrode lose electrons and enter solution as cations A occurs preferentially to electrolysis of water molecules. For example, in several embodiments, the metal electrode is made of lead, copper or silver, or any other metal having similar electrochemical properties.

It will be further appreciated that in cases where the metal cations $A^{+n}$ may interfere with the molecules to be separated by binding to the molecules or by chemically interacting with them, the metal cations can be prevented from reaching the separated molecules by increasing the length of the body of gel matrix 18. This can be accomplished, for example, by increasing the length between the anode 24 and We loading sites 36. In this way, a sufficient degree of separation of the molecules can be achieved before a substantial amount of the metal cations $A^{+n}$ reach the moving front of the separated molecules during the electrophoresis.

It will be further appreciated, that in other cases where the metal cations $A^{+n}$ may interfere with the molecules to be separated by binding to the molecules or by chemically interacting with them, the metal cations can be prevented from reaching the separated molecules by including an electrolyte solution within gel matrix 18 such as but not limited to Bis-Tris-Tricine, Bis-Tris-Bicine, Tris-Glycine, Bis-Tris-Glycilglycine, Amino-methyl propanol-Proline, or TBE. As described above, anode 24 is made of an electrochemically ionizable metal such as but not limited to copper, or silver. As described in the example section hereinbelow, the results of using a specific composition for the electrolyte solutions in combination with ionizable metal, is that the migration of metal ions through the gel matrix 18 is inhibited, and thereby restricted to the area of the anode.

The following examples, which are not intended to limit the scope of the present invention, illustrate how the ion source matrix 22 and the metal electrode 26 are prepared (Examples 1 and 2), and present the results of using a specific composition for the electrolyte solution in combination with ionizable metal for the anode 24 (Examples 3-10).

Example 1

The ion source matrix 22 was prepared as follows:

A. a suspending gel of 3% agarose in 0.4×TAE buffer solution was prepared.

B. 0.6 grams of lead carbonate ($PbCO_3$), prepared by bubbling $CO_2$ into a solution of lead acetate following by filtration and wash by water of the precipitate, were suspended in 2 ml of the 3% agarose suspending gel of step A to obtain the ion source matrix 22.

C. A strip of lead was used as the cathode 26.

Example 2

A. a suspending gel of 3% agarose in 0.4× TAE buffer solution was prepared.

B. 0.3 grams of silver chloride (AgCl) were suspended in 2 ml of the 3% agarose suspending gel of step A to obtain the ion source matrix 22.

C. A strip of aluminum was used as the cathode 26.

Examples 3-10

Gel matrices containing several combinations of electrolyte solution were tested for use with a DNA sample (100 bp+1 kb ladder from Fermentas, Lithuaina) containing a tracking dye, such as bromophenol blue. The gel was run at 90-120V (currents=4-9 mAmps) until the bromophenol blue reached a distance of 5.7 cm from the wells. In these examples, an aluminum cathode was used in combination with a copper anode (Examples 3-8) or a silver anode (Examples 9 and 10). In the following examples, the electrolyte solution concentration was 100 mM, and the size of the cassette in length, width and thickness was 100 mm, 80 mm and 6.7 mm, respectively. Ions generated by the anode during electrophoresis procedure were inhibited when using the conditions describe hereinbelow. This phenomenon is likely caused by the formation of a salt complex.

Example 3

For an electrolyte solution at pH=7, the following components were used:

50 mM Bis-Tris; (bis[2-hydroxyethyl]iminotris[hydroxymethyl]methan), 50 mM Tricine (N-tris[hydroxymethyl]methylglycine), Results: Migration of the copper ions toward the cathode in the gel was inhibited.

Example 4

For an electrolyte solution at pH=7, the following components were used:

50 mM Bis-Tris; 50 mM Bicine (N,N-bis[2-hydroxyethyl]glycine)

Results: Migration of the copper ions toward the cathode in the gel was inhibited.

Example 5

For an electrolyte solution at pH=9.0, the following components were used:

50 mM Tris
50 mM Glycine

Results: Migration of the copper ions toward the cathode in the gel was inhibited.

Example 6

For an electrolyte solution at pH=7, the following components were used:

50 mM Bis-Tris
50 mM Glycilglycine

Results: Migration of the copper ions toward the cathode in the gel was inhibited.

Example 7

For an electrolyte solution at pH=9.5, the following components were used:

50 mM Amino methyl propanol: 50 mM Proline

The migration of the copper ions toward the cathode in the gel was inhibited.

Example 8

For a buffer solution at pH=8.3, 1XTBE (Tris-Borate EDTA (Sigma) –89 mM Tris, 89 mM Borate, 2 mM EDTA Results: Migration of the copper ions toward the cathode in the gel was inhibited.

Example 9

For an electrolyte solution at pH=7, the following components were used:

50 mM Bis-Tris; (bis[2-hydroxyethyl]iminotris[hydroxymethyl]methan), 50 mM Tricine (N-tris[hydroxymethyl]methylglycine), Results: Migration of the silver ions toward the cathode in the gel was inhibited.

Example 10

For a buffer solution at pH=8.3, 1XTBE (Tris-Borate EDTA (Sigma) –89 mM Tris, 89 mM Borate, 2 mM EDTA Results: Migration of the silver ions toward the cathode in the gel was inhibited.

When using the compositions describe hereinabove, the migration of copper and/or silver ions toward the cathode was inhibited. Movement was limited to a distance of about 5 mm from the edge of the copper/silver anode thereby not penetrating the running region of the gel during the running time.

Alternatively, according to another embodiment of the present invention, in order to avoid accumulation of gases during the electrophoresis process, thus allowing the chamber to be sealed, the electrodes comprise gas-absorbing materials.

According to one embodiment of the present invention anode 24 comprises oxygen-absorbing material. In preferred embodiments, anode 24 is made of aluminum or carbon. In another embodiment, cathode 26 comprises hydrogen-absorbing material. In preferred embodiments, cathode 26 is made of palladium, carbon or a metal hydride. In one embodiment of the present invention a plurality of apertures corresponding to plurality of loading sites 36 which are contained within region C may be introduced into gel 18, by using a "comb" having a row of protruding teeth positioned so that the teeth project into the gel layer while it sets. The plurality of apertures and the corresponding plurality of loading sites. When the gel has set, the comb is removed to leave a row(s) of loading sites 36, in the layer. One row or several rows may be formed. In region C the plurality of apertures corresponding to plurality of loading sites 36 are spaced at predetermined intervals so as to conform with spacing intervals among common tips of a loader for simultaneous loading of multiple samples for electrophoresis such as for example a multi-pipette.

Additionally, the apparatus for conducting electrophoresis may include multiple anodes and cathodes for which the anode and the cathode are each composed of materials described hereinabove. It will be appreciated by persons skilled in the art that the present invention is not limited to what has been particularly shown and described hereinabove. Rather, the scope of the present invention is defined only by the claims that follow:

What is claimed is:

1. A disposable cassette for conducting electrophoresis, wherein the cassette comprises:
   i) an enclosed chamber having a top wall, a bottom wall, two side walls, a first end wall and a second end wall, wherein;
      the top wall comprises one or more apertures;
      the bottom wall is contiguous, and
      the chamber comprises a first region, a second region and a third region, wherein the second region is located between the first end wall and the third region, the first region is located between the second end wall and the third region, and the third region is located between the second region and the first region, and wherein the one or more apertures of the top wall are located above and adjacent to the third region;
      and wherein the chamber comprises an electrophoresis area;
   ii) an anode located within either the second region or the first region
   iii) a cathode located within either the second region or the first region, provided that the anode and the cathode are not together in the same region; and
   iv) an electrophoresis gel matrix, said electrophoresis gel matrix comprising one or more wells located below the apertures;
   wherein the electrophoresis gel matrix substantially occupies the first region, the second region and the third region, and wherein at least a portion of the anode is in contact with the electrophoresis gel matrix; and
   wherein the cassette further comprises a matrix, wherein the matrix is in contact with the cathode, and the matrix comprises at least one water sparingly soluble salt; and wherein during the electrophoresis the electrophoresis gel matrix comprises at least one water sparingly soluble salt ion.

2. The disposable cassette of claim 1, wherein the third region is not sealed and either the second region or the first region is sealed, or the third region is not sealed and both the second region and the first region are sealed.

3. The disposable cassette of claim 1, wherein the anode comprises an electrochemically ionizable conducting material, wherein the electrochemically ionizable conducting material is electrochemically ionizable during the electrophoresis.

4. The disposable cassette of claim 3, wherein the electrochemically ionizable conducting material is a metal.

5. The disposable cassette of claim 4, wherein the metal comprises copper.

6. The disposable cassette of claim 4, wherein the metal comprises silver or lead.

7. The disposable cassette of claim 1, wherein the anode comprises an oxygen-absorbing material.

8. The disposable cassette of claim 1, wherein the anode is selected from the group consisting of aluminum and carbon.

9. The disposable cassette of claim 1, wherein the electrophoresis gel matrix is substantially free from oxygen gas during the electrophoresis.

10. The disposable cassette of claim 1, wherein the apertures corresponding to the one or more wells are spaced at predetermined intervals so as to conform with intervals between tips on a multi-pipette loader.

11. The disposable cassette of claim 10, wherein the apertures are arranged in one or more rows.

12. The disposable cassette of claim 10 wherein the apertures are arranged in two or more rows and the rows are arranged in a stagger format.

13. The disposable cassette of claim 1, wherein the cathode comprises a hydrogen-absorbing material.

14. The disposable cassette of claim 1, wherein the cathode is selected from the group consisting of palladium, carbon and metal hydrides.

15. The disposable cassette of claim 1, wherein the electrophoresis gel matrix is substantially free from hydrogen gas during the electrophoresis.

16. The disposable cassette of claim 3, wherein the electrolyte is of a composition that inhibits the migration of ions generated during an electrochemical reaction of the electrochemically ionizable conducting material.

17. The disposable cassette of claim 16, wherein the electrolyte is selected from the group consisting of Bis-Tris-Tricine, Bis-Tris-Bicine, Tris-Glycine, Bis-Tris-Glycilglycine, Amino methyl propanol-Proline, and Tris-Borate EDTA (TBE).

18. The disposable cassette of claim 1, wherein the at least one anode is located within the second region and the at least one cathode is located within the first region.

19. The disposable cassette of claim 1, wherein the at least one anode is located within the first region and the at least one cathode is located within the second region.

20. The disposable cassette of claim 1, wherein the at least one anode or the at least one cathode is embedded within the electrophoresis gel matrix.

21. The disposable cassette of claim 1, wherein the electrophoresis gel matrix further comprises ions generated during an electrochemical reaction of the anode during the electrophoresis.

22. The disposable cassette of claim 1, wherein the electrolyte is of a composition that inhibits the migration of ions generated during the electrochemical reaction of the anode.

23. The disposable cassette of claim 1, wherein the at least one anode and the at least one cathode are embedded within the electrophoresis gel matrix.

24. The disposable cassette of claim 23, wherein the electrolyte is selected from the group consisting of Bis-Tris-Tricine, Bis-Tris-Bicine, Tris-Glycine, Bis-Tris-Glycilglycine, Amino methyl propanol-Proline, and Tris-Borate EDTA (TBE).

25. The disposable cassette of claim 1, wherein the top wall is sealed to the side walls.

26. The disposable cassette of claim 25, wherein the top wall is sealed to the to the first end wall and the second end wall.

27. The disposable cassette of claim 1, wherein the bottom wall is flat.

28. The disposable cassette of claim 1, further comprising a comb having one or more teeth protruding through the one or more apertures into the electrophoresis gel matrix.

29. The disposable cassette of claim 1, wherein the electrolyte comprises Bis-Tris/Tricine, Bis-Tris/Bicine, Tris-Glycine, Bis-Tris-Glycilglycine, Amino methyl propanol/Proline, or Tris-Borate EDTA (TBE).

30. The disposable cassette of claim 18, wherein the anode comprises an electrochemically ionizable metal.

31. The disposable cassette of claim 19, wherein the anode comprises an electrochemically ionizable metal.

32. The disposable cassette of claim 30, wherein the electrochemically ionizable metal comprises copper.

33. The disposable cassette of claim 30, wherein the electrochemically ionizable metal comprises silver.

34. The disposable cassette of claim 22, wherein the electrophoresis gel matrix is substantially free from oxygen gas during the electrophoresis.

35. The disposable cassette of claim 25, wherein the electrolyte is selected from the group consisting of Bis-Tris-Tricine, Bis-Tris-Bicine, Tris-Glycine, Bis-Tris-Glycilglycine, Amino methyl propanol-Proline, and Tris-Borate EDTA (TBE).

36. The disposable cassette of claim 1, wherein the electrophoresis gel matrix comprises sufficient ions for performing electrophoresis.

37. A method for performing electrophoresis, the method comprising the steps of:
   i) providing a disposable cassette, wherein the cassette comprises:
      an enclosed chamber having a top wall, a bottom wall, two side walls, a first end wall and a second end wall, wherein;
      the top wall comprises one or more apertures;
      the bottom wall is contiguous, and
      the chamber comprises a first region, a second region and a third region,
      wherein the second region is located between the first end wall and the third region, the first region is located between the second end wall and the third region, and the third region is located between the second region and the first region, and wherein the one or more apertures of the top wall are located above and adjacent to the third region;
         and wherein the chamber comprises an electrophoresis area;
      an anode located within the second region or the first region;
      a cathode located within the second region or the first region, provided that the anode and the cathode are not together in the same region;
      an electrophoresis gel matrix, said electrophoresis gel matrix comprising one or more wells located below the apertures;
      wherein the electrophoresis gel matrix substantially occupies the first region, the second region and the third region, and wherein at least a portion of the anode and the cathode are in contact with the electrophoresis gel matrix; and
   ii) loading one or more samples into the one or more wells through the one or more apertures;
   iii) applying an electrical field to the electrophoresis gel matrix thereby performing electrophoresis; and
   iv) degrading a sparingly water-soluble salt in contact with the at least one cathode by the application of the electrical field thereby releasing ions required for maintaining the electrical field.

38. The method of claim 37, further comprising the step of degrading the anode by the application of the electrical field, thereby releasing ions required for maintaining the electrical field, wherein the anode comprises an electrochemically ionizable conducting material.

39. The method of claim 38, wherein the electrolyte is of a composition that inhibits migration of ions generated during the step of degrading the anode by the application of the electrical field.

40. The method of claim 39, wherein the electrolyte is selected from the group consisting of Bis-Tris-Tricine, Bis-Tris-Bicine, Tris-Glycine, Bis-Tris-Glycilglycine, Amino methyl propanol-Proline, and Tris-Borate EDTA (TBE).

41. The method of claim 37, wherein the third region is not sealed and either the second region or the first region is sealed before and during performing the electrophoresis, or the first region is not sealed and both the second region and the first region are sealed before and during performing the electrophoresis.

42. The method of claim 37, wherein the top wall is sealed to the side walls before and during performing electrophoresis.

43. The method of claim 42, wherein the top wall is sealed to the to the first end wall and the second end wall before and while performing electrophoresis.

44. The method of claim 37, wherein the bottom wall is flat.

45. The method of claim 37, wherein the electrolyte comprises Bis-Tris/Tricine, Bis-Tris/Bicine, Tris-Glycine, Bis-Tris-Glycilglycine, Amino methyl propanol/Proline, or Tris-Borate EDTA (TBE).

46. The method of claim 41, wherein the electrolyte is selected from the group consisting of Bis-Tris-Tricine, Bis-Tris-Bicine, Tris-Glycine, Bis-Tris-Glycilglycine, Amino methyl propanol-Proline, and Tris-Borate EDTA (TBE).

47. The method of claim 46, wherein the apertures corresponding to the one or more wells are spaced at predetermined intervals so as to conform with intervals between tips on a multi-pipette loader.

48. The method of claim 46, wherein the apertures corresponding to the one or more wells are arranged in one or more rows.

49. The method of claim 46, wherein the apertures are arranged in two or more rows and the rows are arranged in stagger format.

50. A method for electrophoresis, the method comprising the steps of: applying an electrical field to a gel comprising one or more wells, wherein the gel is contained within a disposable cassette comprising one or more apertures; degrading a metal anode by said application of said electrical field; releasing ions required for maintaining an electrical field by said degradation, and inhibiting migration of said ions in the vicinity of said anode.

* * * * *